(12) United States Patent
Seto

(10) Patent No.: US 10,194,789 B2
(45) Date of Patent: Feb. 5, 2019

(54) ROLLING SHUTTER IMAGING DEVICE AND ENDOSCOPE APPARATUS INCLUDING THE SAME

(71) Applicant: FUJIFILM Corporation, Tokyo (JP)

(72) Inventor: Yasuhiro Seto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1169 days.

(21) Appl. No.: 14/472,606

(22) Filed: Aug. 29, 2014

(65) Prior Publication Data

US 2014/0371535 A1 Dec. 18, 2014

Related U.S. Application Data

(63) Continuation of application No. PCT/JP2013/058943, filed on Mar. 27, 2013.

(30) Foreign Application Priority Data

| Mar. 28, 2012 | (JP) | ................................. 2012-074245 |
| Feb. 26, 2013 | (WO) | .................. PCT/JP2013/054975 |
| Mar. 11, 2013 | (JP) | ................................. 2013-047904 |

(51) Int. Cl.
*A61B 1/06* (2006.01)
*A61B 1/07* (2006.01)
(Continued)

(52) U.S. Cl.
CPC .......... *A61B 1/045* (2013.01); *A61B 1/00006* (2013.01); *A61B 1/00009* (2013.01);
(Continued)

(58) Field of Classification Search
CPC . A61B 1/045; A61B 1/00006; A61B 1/00009; A61B 1/0661; G02B 23/2461; G02B 23/2484
(Continued)

(56) References Cited

U.S. PATENT DOCUMENTS 8,668,639 B2 * 3/2014 Kagaya .................. A61B 1/045
348/68
2006/0256207 A1 11/2006 Kokubo et al.
(Continued)

FOREIGN PATENT DOCUMENTS

JP 2005-270266 A 10/2005
JP 2007-318581 A 12/2007
(Continued)

OTHER PUBLICATIONS

Japanese Office Action, dated Jul. 25, 2017, for Japanese Application No. 2016-175567, along with an English machine translation.
(Continued)

*Primary Examiner* — John P Leubecker
*Assistant Examiner* — William Chou
(74) *Attorney, Agent, or Firm* — Birch, Stewart, Kolasch & Birch, LLP

(57) ABSTRACT

A wide dimming dynamic range and high dimming resolution are obtained without causing a variation in the amount of received light due to pulse illumination light in each line of an imaging element. An imaging device includes a light source emitting light by pulse driving, a light source control unit controlling the amount of emitted light by performing pulse modulation driving of the light source, and an imaging unit including an imaging element, in which a plurality of pixels are arrayed in a horizontal and vertical direction, and performs imaging by driving the imaging element using a rolling shutter method. The light source control unit performs pulse driving of the light source at a timing synchronized with a timing pulse signal having, as a period, 1/p (p is an integer of 1 or more) of the exposure start timing interval when driving the imaging element using the rolling shutter method.

20 Claims, 15 Drawing Sheets

(51) Int. Cl.
  *H04N 5/225* (2006.01)
  *A61B 1/04* (2006.01)
  *A61B 1/045* (2006.01)
  *A61B 1/00* (2006.01)
  *G02B 23/24* (2006.01)

(52) U.S. Cl.
  CPC ........ *A61B 1/0661* (2013.01); *G02B 23/2461* (2013.01); *G02B 23/2484* (2013.01); *H04N 5/225* (2013.01); *A61B 1/04* (2013.01); *A61B 1/06* (2013.01); *H04N 2005/2255* (2013.01)

(58) Field of Classification Search
  USPC ....... 600/109, 110, 160, 178, 180, 181, 182; 348/45, 65, 68, 69, 70
  See application file for complete search history.

(56) References Cited

U.S. PATENT DOCUMENTS

2008/0050109 A1    2/2008   Noyes et al.
2008/0262299 A1   10/2008   Niida et al.
2012/0016200 A1*   1/2012   Seto .................... A61B 1/0653
                                                            600/180
2014/0225998 A1*   8/2014   Dai ..................... H04N 5/2354
                                                            348/65

FOREIGN PATENT DOCUMENTS

JP      2008-264252 A    11/2008
JP      2010-501898 A     1/2010
JP         2012-19983 A   2/2012
WO   WO 2005/091624 A1   9/2005

OTHER PUBLICATIONS

International Preliminary Examination Report for PCT/JP2013/058943 dated Mar. 7, 2014.
International Search Report for PCT/JP2013/058943 dated Jun. 11, 2013.
Written Opinion of the International Searching Authority for PCT/JP2013/058943 dated Jun. 11, 2013.
Japanese Notification of Reasons for Refusal and English translation thereof, dated Apr. 19, 2016, for corresponding Japanese Application No. 2013-047904.

* cited by examiner

ROLLING SHUTTER IMAGING DEVICE AND ENDOSCOPE APPARATUS INCLUDING THE SAME

CROSS-REFERENCE TO RELATED APPLICATIONS

This application is a Continuation of PCT International Application No. PCT/JP2013/058943 filed on Mar. 27, 2013, which claims priority under 35 U.S.C. § 119(a) to Patent Application No. 2012-074245 filed in Japan on Mar. 28, 2012, Patent Application No. 2013-047904 filed in Japan on Mar. 11, 2013, and PCT International Application No. PCT/JP2013/054975 filed on Feb. 26, 2013, all of which are hereby expressly incorporated by reference into the present application.

BACKGROUND OF THE INVENTION

1. Field of the Invention

The present invention relates to an imaging device and an endoscope apparatus including the same.

2. Description of the Related Art

A general endoscope apparatus generates an observation image by emitting white light from a white light source such as a xenon lamp, as illumination light, to an observation area in a body cavity through a light guide and capturing reflected light images due to the emission of the white light using an imaging element. The imaging element includes an electronic shutter, and adjusts the amount of received light by controlling an increase or decrease in the charge accumulation time using the electronic shutter. In the endoscope apparatus, light amount information is extracted from an image signal output from the imaging element, and the exposure time (shutter speed) by the electronic shutter is controlled based on the light amount information. For example, when the extracted light amount information is smaller than a reference value, the shutter speed is reduced to increase the amount of received light. In contrast, when the light amount information is larger than the reference value, the shutter speed is increased to reduce the amount of received light amount. As a result, since exposure according to the illumination light intensity and the observation target is performed, the brightness of the captured image can be maintained satisfactorily (refer to JP2005-270266A).

In recent years, instead of a white light source such as a xenon lamp, a semiconductor light source such as a laser light source or an LED light source has been adopted as a light source due to high efficiency and easy maintenance. Also for the imaging element, a complementary metal oxide semiconductor (CMOS) type image sensor having lower power consumption and higher reading speed than a charge coupled device (CCD) type imaging element has been adopted.

SUMMARY OF THE INVENTION

An MOS type imaging element, such as the CMOS type image sensor, is usually driven by a rolling shutter method. The rolling shutter method is a method of starting the accumulation of electric charges and reading the accumulated electric charges by performing an exposure operation sequentially for at least one or more scanning lines or each pixel, that is, performing resetting sequentially for each scanning line or pixel in an MOS type imaging element (also referred to as a focal plane shutter method). Unlike a global shutter type imaging element in which the simultaneity of exposure periods is maintained, the rolling shutter type imaging element has a characteristic that the exposure start timing is shifted for each line according to the scanning timing of each line of the imaging surface. For this reason, there is no problem when exposure is performed under the illumination light that is continuously lit with a fixed amount of light. However, when exposure is performed under the illumination light of a pulsed light source, such as a semiconductor light source, the amount of received light may be changed for each line. In this case, a captured image with brightness unevenness in which each line has different brightness is obtained.

When using a pulsed light source, such as a semiconductor light source, the amount of emitted light is controlled by pulse modulation, such as pulse width modulation (PWM). However, in the driving using only the same modulation method, a dimming dynamic range may be insufficient. Accordingly, dimming resolution may be insufficient in the area of a low amount of light. In addition, when the exposure time by the shutter is fixed to the maximum exposure time, a fast moving subject may be blurred. Thus, when imaging is performed using a rolling shutter type imaging element under the illumination light from the pulsed light source, neither the necessary and sufficient image quality nor dimming performance can be obtained.

Therefore, it is an object of the present invention to provide an imaging device, which can realize both a wide dimming dynamic range and high dimming resolution without causing a variation in the amount of received light due to pulse illumination light in each line of an imaging element when performing imaging under the illumination light of a pulsed light source using a rolling shutter type imaging element, and an endoscope apparatus including the imaging device.

The present invention is configured as follows.

(1) An imaging device including: a light source that emits light by pulse driving; a light source control unit that controls an amount of light emitted from the light source by performing pulse modulation driving of the light source; and an imaging unit that includes an imaging element, in which a plurality of pixels are arrayed in a horizontal direction and a vertical direction, and performs imaging by driving the imaging element using a rolling shutter method. The light source control unit performs pulse driving of the light source at a timing synchronized with a timing pulse signal having, as a period, $1/p$ (p is an integer of 1 or more) of an exposure start timing interval when driving the imaging element using the rolling shutter method.

(2) An endoscope apparatus including the imaging device described above.

According to the present invention, it is possible to realize both a wide dimming dynamic range and high dimming resolution without causing a variation in the amount of received light due to pulse illumination light in each line of an imaging element when performing imaging under the illumination light that is pulse emission driven using a rolling shutter type imaging element.

DESCRIPTION OF THE PREFERRED EMBODIMENTS

Figure 1:
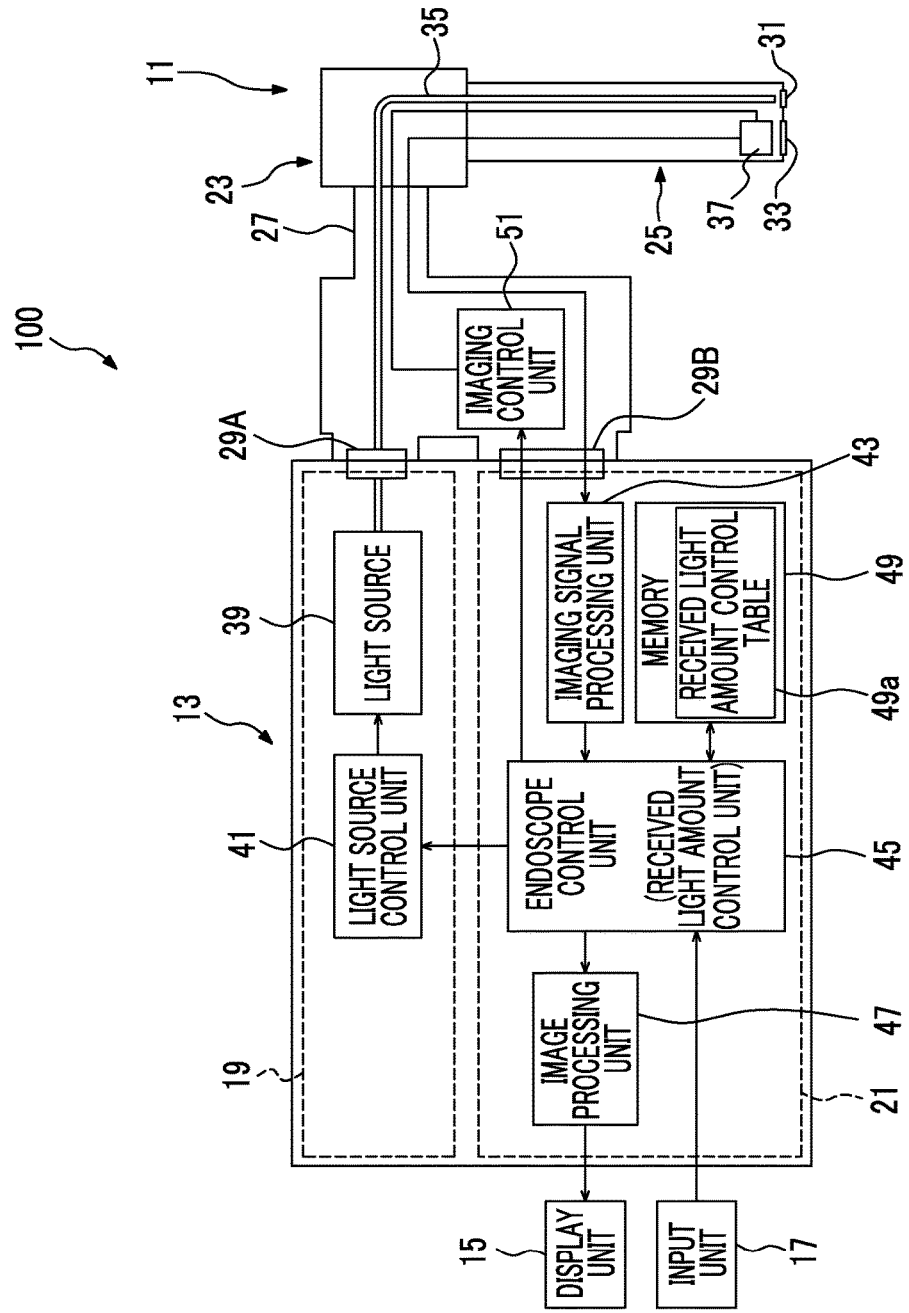
FIG. 1 is a diagram for explaining an embodiment of the present invention, and is a block diagram showing the schematic configuration of an endoscope apparatus.
Figure 2:
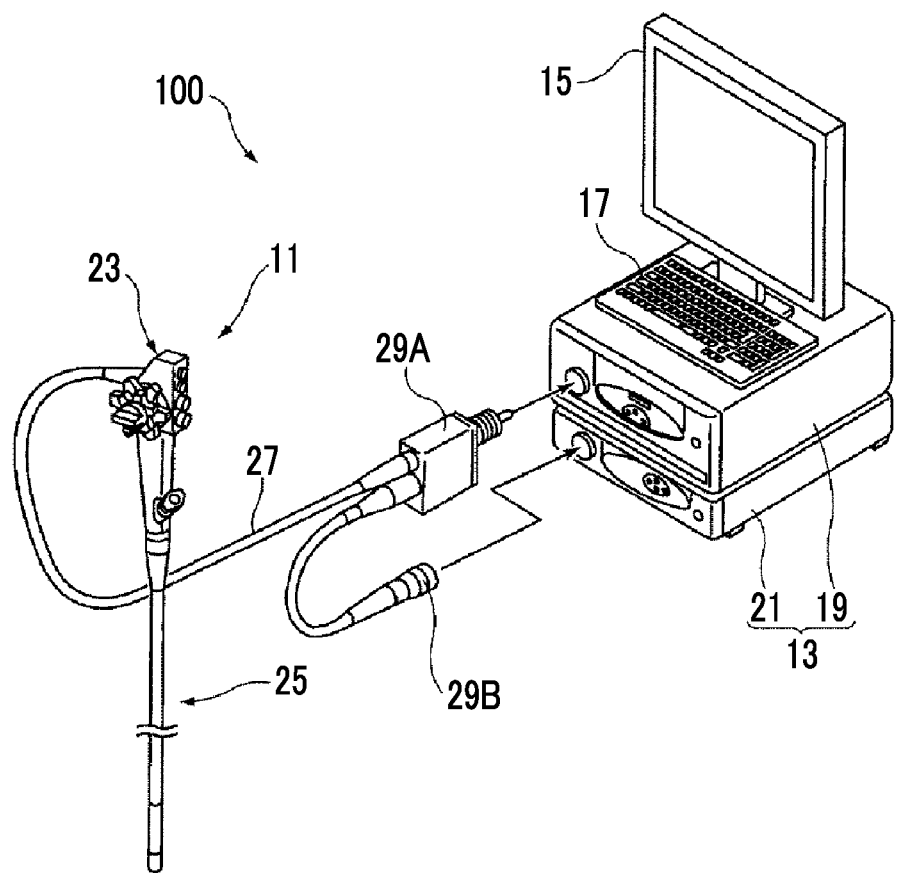
FIG. 2 is an external view showing an example of the specific configuration of the endoscope apparatus.

Hereinafter, an embodiment of the present invention will be described in detail with reference to the diagrams. FIG. 1 is a diagram for explaining the embodiment of the present invention, and is a block diagram showing the schematic configuration of an endoscope apparatus. FIG. 2 is an external view showing an example of the specific configuration of the endoscope apparatus.

<Configuration of the Endoscope Apparatus>

As shown in FIGS. 1 and 2, an endoscope apparatus 100 includes an endoscope 11, a control device 13 to which the endoscope 11 is connected, a display unit 15 connected to the control device 13, such as a liquid crystal monitor, and an input unit 17 to input information to the control device 13, such as a keyboard or a mouse. The control device 13 is configured to include a light source device 19 that generates illumination light and a processor 21 that performs signal processing or the like on a captured image.

The endoscope 11 includes a body operation unit 23 and an insertion unit 25 that is provided continuously to the body operation unit 23 and is inserted into the body cavity. The body operation unit 23 is connected to a universal code 27. The universal code 27 has a distal end divided into two parts. A light guide connector 29A provided at one distal end is connected to the light source device 19, and a video connector 29B provided at the other distal end is connected to the processor 21.

An illumination window 31 and an observation window 33 are provided at the distal end of the insertion unit 25 of the endoscope 11 opposite the body operation unit 23. The illumination window 31 emits illumination light guided through a light guide 35 toward a subject, and the observation window 33 provides an observed image to an imaging element 37.

The light source device 19 includes a light source 39 that emits light by pulse driving and a light source control unit 41 that controls the amount of light, which is emitted from the light source 39, by pulse emission driving. Light emitted from the light source 39 is introduced into a light guide 35.

The processor 21 includes an imaging signal processing unit 43, an endoscope control unit 45, an image processing unit 47, and a memory 49. The endoscope 11 includes an imaging control unit 51 for controlling the driving of the imaging element 37. The imaging control unit 51 controls the driving of the imaging element 37 according to an instruction from the endoscope control unit 45. The imaging element 37 generates a captured image by imaging reflected light from the subject of the illumination light, which is irradiated from the illumination window 31, through the observation window 33 and a lens (not shown). The imaging element 37 outputs an image signal of the generated observation image to the processor 21.

The endoscope control unit 45 is connected to the memory 49 as storage means for storing an observation image or various kinds of information, which will be described later, and the image signal output from the imaging signal processing unit 43 is subjected to appropriate image processing by the image processing unit 47 and is output to the display unit 15 as an image. In addition, the endoscope control unit 45 is connected to a network such as a LAN (not shown), and controls the entire endoscope apparatus 100 (for example, delivers information including image data).

The imaging element 37 is a CMOS type image sensor driven by a so-called rolling shutter method. The observation image formed and captured on the light receiving surface of the imaging element 37 is converted into an electrical signal, and the electrical signal is input to the imaging signal processing unit 43 of the processor 21 and is converted into a video signal. Although described in detail later, the imaging signal processing unit 43 also functions as light amount detection means for detecting the light amount of a subject image based on the imaging signal output from the imaging element 37.

The light source 39 includes one or more laser light sources that are semiconductor light emitting elements. The light source 39 may emit only specific wavelength light or emit light beams of a plurality of wavelengths simultaneously in addition to generating white light. The light source that generates white light can be configured to include a laser light source, which outputs blue laser light having a center wavelength of 445 nm, and a wavelength conversion member including a plurality of types of phosphors (for example, phosphors including a YAG-based phosphor or a phosphor containing BAM ($BaMgAl_{10}O_{37}$)) that absorb a part of the blue laser light and perform excitation and emission of green to yellow. However, the present invention is not limited thereto.

As this laser light source, for example, a broad area type InGaN-based laser diode can be used. According to the configuration described above, blue laser light from the laser light source and excitation light of green to yellow, which is obtained by wavelength conversion of the blue laser light, are combined to generate white light. The intensity of light emitted from the light source 39 is arbitrarily adjusted by pulse modulation driving.

A wavelength conversion member (not shown) is disposed in the light source 39, and white light from the wavelength conversion member is guided to the illumination window 31, which is disposed at the distal end of the endoscope insertion unit 25, through the light guide 35 formed of a fiber bundle including a large number of fibers.

The light source 39 can generate illumination light suitable for the observation of capillaries or fine patterns of the living tissue surface layer by providing, for example, a laser light source that outputs laser light having a center wavelength of 405 nm in addition to the laser light source for the white light described above. In this case, the light source 39 may be configured to use mixed light, which is irradiated by simultaneously emitting laser light having a center wavelength of 405 nm and white light based on laser light having a center wavelength of 445 nm at an arbitrary intensity ratio, as illumination light for endoscopic observation.

The light source 39 may also be configured such that the wavelength conversion member is disposed at a position closest to the illumination window 31. In this case, it is possible to adopt a configuration in which one or more single-mode optical fibers are provided along the endoscope insertion unit 25 and light of the light emitting end is emitted toward the wavelength conversion member. Accordingly, it is possible to reduce the diameter of the endoscope insertion unit.

The light source 39 may also be formed by a light emitting diode instead of the laser light source. In addition, desired wavelength light may be obtained by combining color filters that extract white light and specific wavelength light selectively.

<Control of the Amount of Received Light>

Next, a procedure when the endoscope apparatus 100 configured as described above sets the target amount of received light, by which the imaging element receives light, and controls the light source 39 and the imaging element 37 so that the set target amount of received light is obtained will be described.

The imaging signal processing unit 43 provided in the processor 21 shown in FIG. 1 receives RAW data output from the imaging element 37 of the endoscope 11 connected to the processor 21. The imaging signal processing unit 43 outputs a control signal, which is for controlling the amount of light emitted from the light source 39, from the endoscope control unit 45 to the light source control unit 41 and a control signal, which is for controlling the imaging element 37 at the optimal shutter speed, from the endoscope control unit 45 to the imaging control unit 51 so that the optimal amount of received light (brightness value detected by the imaging element) corresponding to the RAW data is obtained.

Figure 3:
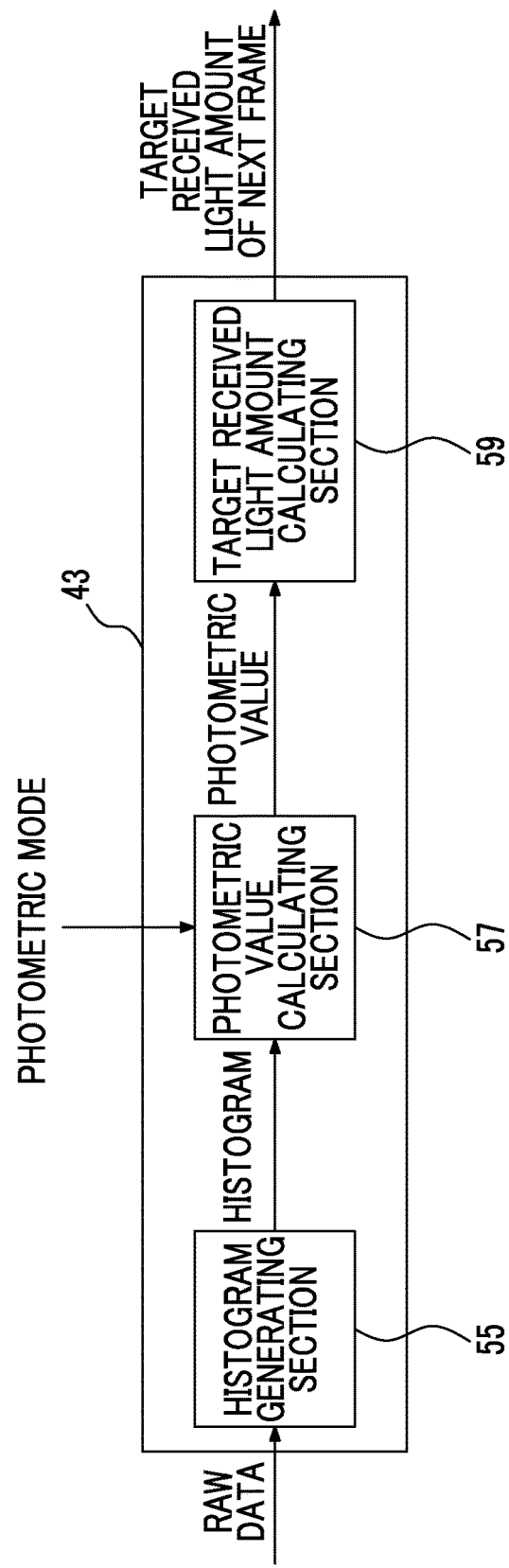
FIG. 3 is a control block diagram of an imaging signal processing unit.

FIG. 3 shows a control block diagram according to the imaging signal processing unit 43. The RAW data (information of a raw image) output from the imaging element 37 is input to a histogram generating section 55. The histogram generating section 55 generates a histogram of the amount of light corresponding to the RAW data, and outputs the histogram to a photometric value calculating section 57. The photometric value calculating section 57 calculates a photometric value based on the generated histogram and a brightness detection value calculated according to various photometric modes (a peak value, an average value, and the like). Then, a target light amount calculating section 59 calculates the target amount of received light of the next frame according to the calculated photometric value. Here, the target amount of received light is a control parameter that is expressed by, for example, 12-bit grayscale (0 to 4096), and is set to a value higher than the current target light amount value when the photometric value is higher than the reference value. The endoscope apparatus 100 selects various control patterns, which will be described later, according to the control parameter expressed as the target amount of received light.

The endoscope control unit 45 shown in FIG. 1 determines each control signal output to the light source control unit 41 and the imaging control unit 51 based on the target amount of received light, which is output from the imaging signal processing unit 43, with reference to a received light amount control table stored in the memory 49. Then, the endoscope control unit 45 functions as a received light amount control unit that controls the amount of received light of the imaging element by driving the light source 39 and the imaging element 37 based on each determined control signal. For example, when the brightness detected by the imaging element is reduced due to the state of the subject, control is performed such that the detected brightness becomes the target brightness by changing the amount of received light, which is larger than the amount of received light corresponding to the combination of the current amount of emitted light and the exposure time, to the target amount of received light. Not only does the endoscope control unit 45 have the functional configuration described above, but also the light source control unit 41 may be made to have a driving pulse generation function based on the received light amount control table and an emission intensity signal of the light source 39 may be output from the endoscope control unit 45 to the light source control unit 41.

A received light amount control table 49a defines the amount of received light of the imaging element 37 by defining the relationship of the brightness according to the reflectance or distance of the subject image, the amount of light emitted from the light source 39, and the shutter speed of the electronic shutter of the imaging element 37. In the received light amount control table 49a, a control pattern to optimize a light source driving signal and shutter speed as control variables for the target amount of received light is set by experimental and analytical methods or a rule of thumb. The received light amount control table 49a is stored in the memory 49.

Figure 4:
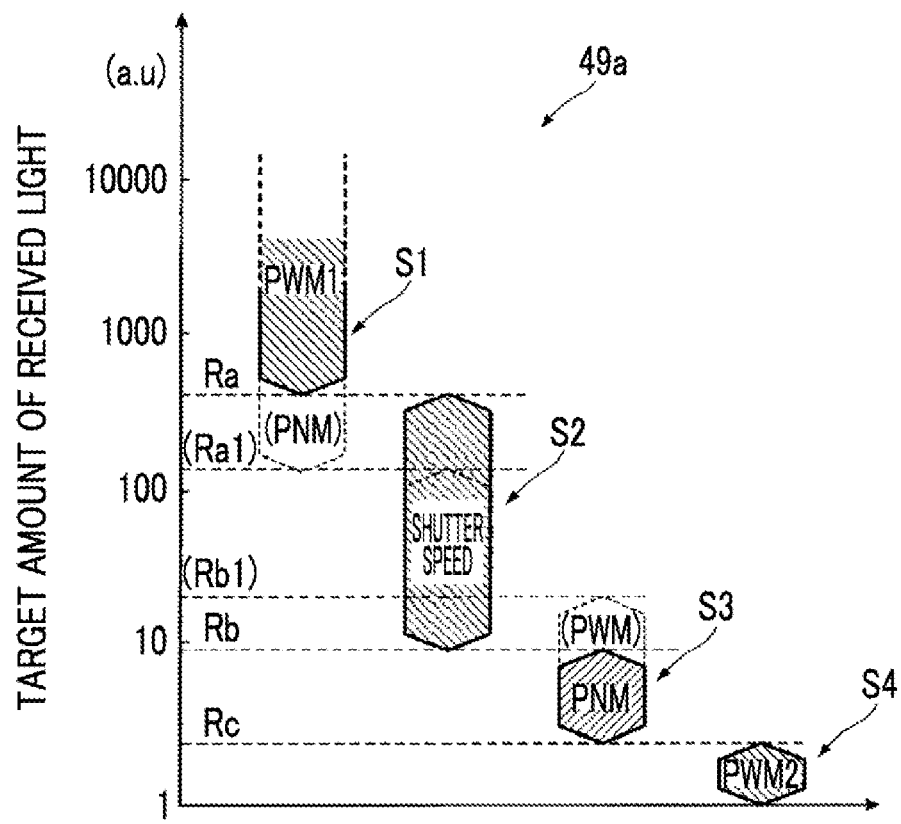
FIG. 4 is an explanatory diagram schematically showing the content of a received light amount control table.

FIG. 4 schematically shows the content of the received light amount control table in this configuration example. The received light amount control table 49a is a table in which the combination of the amount of light emitted from the light source 39 and the exposure time of the imaging element 37 is matched with the amount of received light of the imaging element 37, and is expressed by the control pattern of the amount of light emitted from the light source 39 for the target amount of received light and the control pattern of the shutter speed of the imaging element 37. Each control pattern is formed by control signals or control parameters of each unit for acquiring the target value of the amount of emitted light for the target amount of received light, the target value of the shutter speed of the imaging element, and the like.

The received light amount control table 49a has control areas set such that the amount of received light decreases in an order of a first pulse width control area (PWM1) S1 where the exposure time of the imaging element is fixed and the pulse width of the pulse driving signal output to the light source 39 is increased or decreased, a shutter speed control area S2 where the pulse width of the pulse driving signal of the light source 39 is fixed and the exposure time of the imaging element 37 is increased or decreased, a pulse number control area (pulse number modulation: PNM) S3 where the number of pulses of the pulse driving signal is increased or decreased in a state where the exposure time is fixed to n times (n is an integer of 2 or more) the horizontal scanning period, and a second pulse width control area (PWM2) S4 where the pulse width of the pulse driving signal is increased or decreased in a state where the exposure period is fixed to an integral multiple of n times the horizontal scanning period and the pulse driving signal of the light source is thinned out.

The control pattern in each control area is the first pulse width control area S1 when the target amount of received light is the maximum, and the first pulse width control area S1 and the shutter speed control area S2 are switched to the target amount of received light Ra when the target amount of received light is reduced. When the target amount of received light is further reduced, the shutter speed control area S2 and the pulse number control area S3 are switched to the target amount of received light Rb, and the pulse number control area S3 and the second pulse width control area S4 are switched to the target amount of received light Rc.

The above-described light amount control is to perform pulse driving of the light source 39 at a timing synchronized with a timing pulse signal having 1/p (p is an integer of 1 or more) of the exposure start timing interval of the imaging element as a period.

Next, the above received light amount control will be described in detail.

Figure 5:
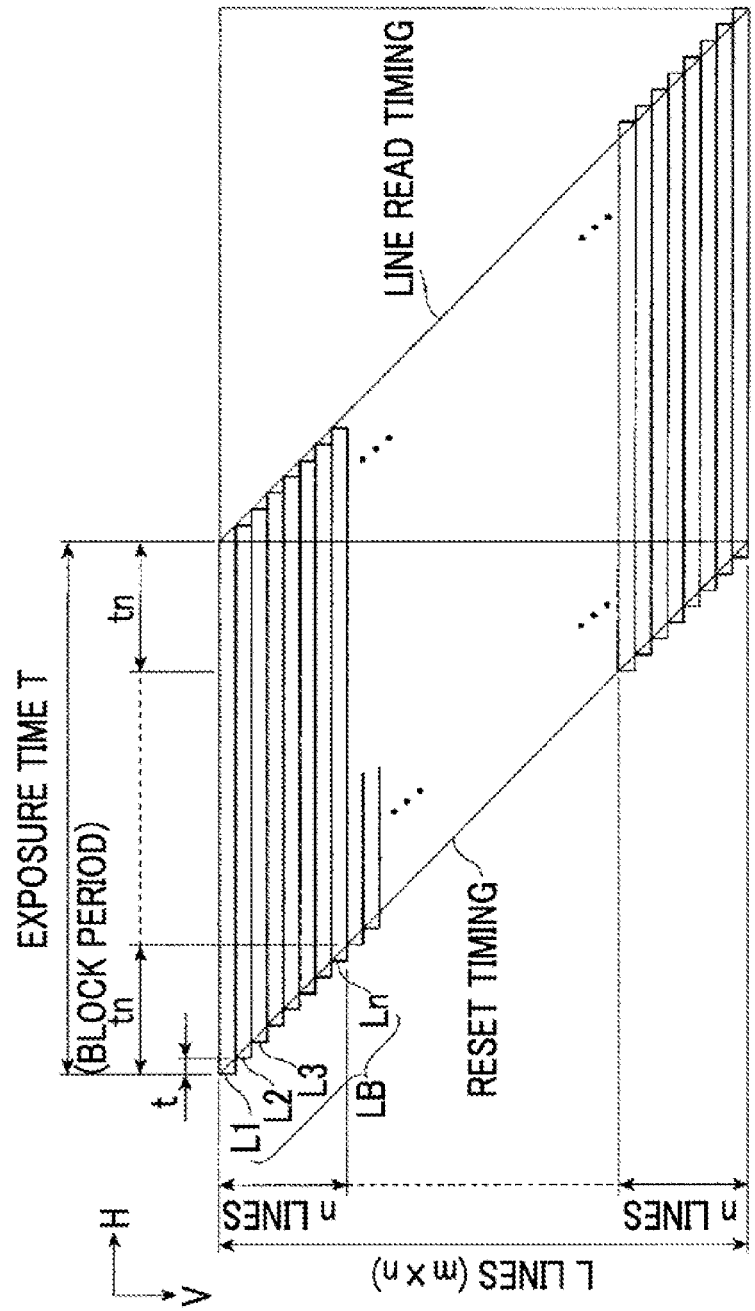
FIG. 5 is a schematic explanatory diagram showing the exposure timing of an imaging element according to a rolling shutter method.

FIG. 5 is a schematic explanatory diagram showing the exposure timing of the imaging element according to the rolling shutter method.

In the rolling shutter method, when respective horizontal pixel lines L1, L2, . . . aligned in a horizontal direction H are sequentially scanned in a vertical direction V from the upper end line to the lower end line in a pixel area of an imaging element in which pixels formed by a number of photoelectric conversion elements are arrayed in the horizontal direction H and the vertical direction V, the exposure start timing of the respective horizontal pixel lines L1, L2, . . . is set so as to be shifted in a direction, in which the exposure start timing is delayed by a horizontal scanning period t sequentially from the upper end line on one end side in the vertical direction. The horizontal scanning period t is a time required per line, which is required for instruction on a logic circuit such as reset and accumulated charge line reading, for one line of one horizontal pixel line (hereinafter, may be simply referred to as a line), and is expressed as an exposure start time difference between the lines L1 and L2 shown in FIG. 5.

Now, a line block LB including n lines, which are obtained by dividing the total number of horizontal pixel lines by an arbitrary integer m (m is an integer of 2 or more), will be defined. For example, if the total number of lines is 1024 lines and n=8 lines, 128 line blocks LB are present. An exposure time T for each of the lines L1, L2, . . . , Ln of the line block LB is set to the length that is divisible by a block period tn obtained by multiplying the horizontal scanning period t by n.

That is, assuming that the number of lines of one line block LB is n lines and m line blocks LB are present, the total number of lines L of one frame is an integral multiple of n. A shift of the exposure start timing between one line block LB and the subsequent line block LB having the same number of lines is the block period tn. Accordingly, the exposure time T of each of the lines L1, L2, . . . , Ln is an integral multiple of the block period tn.

Figure 6:
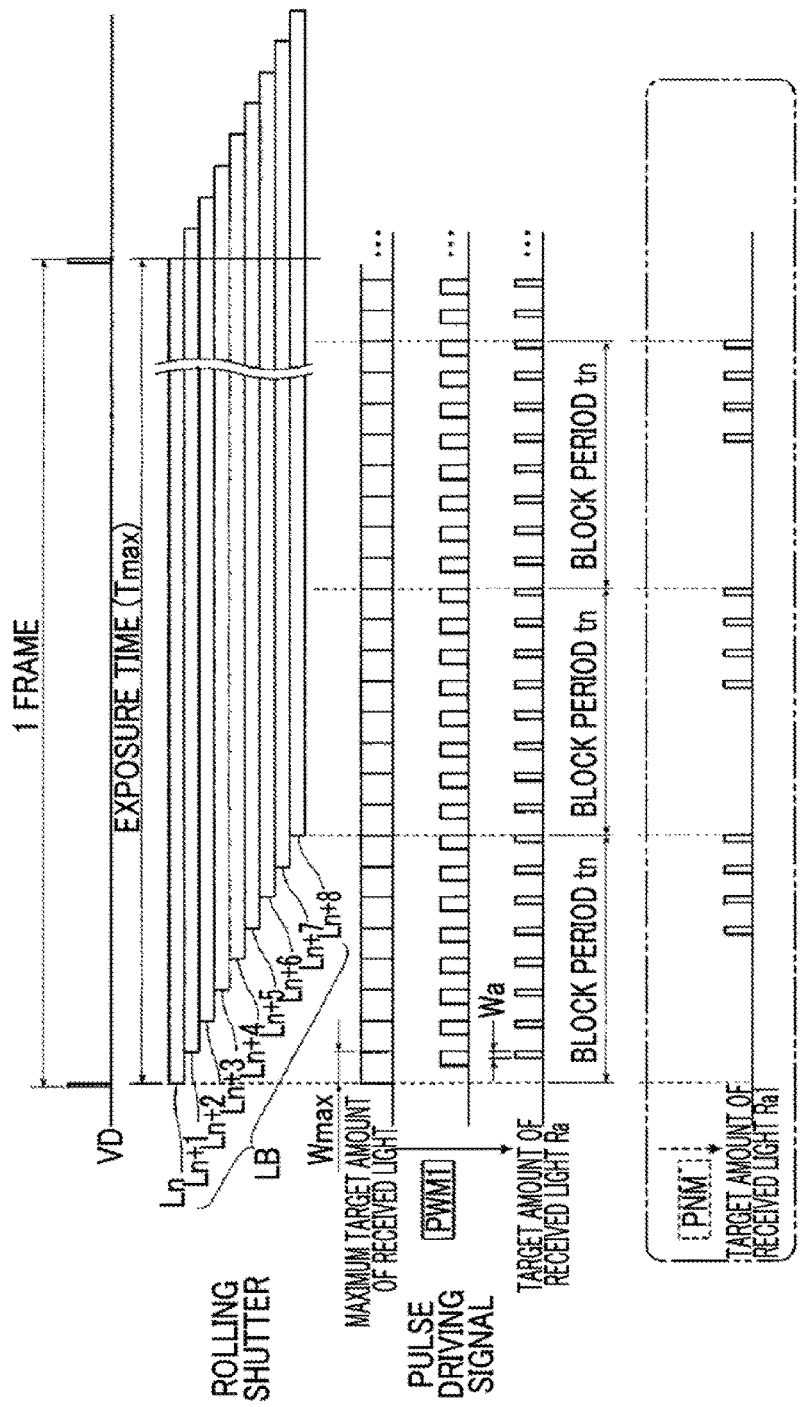
FIG. 6 is an explanatory diagram showing the relationship between the exposure time and the pulse driving signal in a first pulse width control area (PWM1) S1.

FIG. 6 is an explanatory diagram showing the relationship between the exposure time and the pulse driving signal in the first pulse width control area (PWM1) S1. When the target amount of received light is an area of Ra from the maximum value, the endoscope control unit 45 sets the exposure time of the rolling shutter to a maximum exposure time Tmax, which is the same for all lines, in one frame defined by a vertical synchronization signal VD as a television signal. FIG. 6 shows only one line block LB among all lines in one frame.

When the target amount of received light is a maximum value, the endoscope control unit 45 sets a pulse driving signal for driving the light source 39 so as to have a maximum pulse width Wmax and makes the light source 39 remain lit continuously. The pulse driving signal is a pulse signal of the same pattern having the block period tn, which is n times the horizontal scanning period t, as one period, and the endoscope control unit 45 outputs the pulse driving signal in synchronization with the exposure start timing of the head line in the line block LB. The pulse driving signal is repeatedly output while at least one of all lines of the imaging element is set to the exposure time.

In the area of the target amount of received light from the maximum value to Ra, the endoscope control unit 45 fixes the exposure time of the rolling shutter to the maximum exposure time Tmax, and performs pulse width modulation of each pulse of the pulse driving signal for the target amount of received light. For example, a pulse width Wa at the time of the target amount of received light Ra is set to 20% of the maximum pulse width Wmax. The number of pulses of the pulse driving signal in this case is set to n within the block period tn. That is, the horizontal scanning period t is a pulse width equivalent to 100% of one pulse. Thus, since the amount of light emitted from the light source 39 is preferentially reduced on the maximum side of the target amount of received light, it is possible to suppress power consumption.

In addition, when the target amount of received light is much lower than Ra, the endoscope control unit 45 may perform pulse number control to reduce the number of pulses of the pulse driving signal until the target amount of received light reaches Ra1, without performing the control of the shutter speed control area S2 to be described next. That is, in a state where the exposure time of the imaging element is fixed to the same exposure time as the exposure time in the first pulse width control area S1 and the pulse width of the pulse driving signal of the light source 39 is fixed, a second pulse number control area matched with the amount of received light when increasing or decreasing the number of pulses of the pulse driving signal of the light source 39 is set. The amount of received light in the second pulse number control area is between the amount of received light in the first pulse width control area S1 and the amount of received light in the shutter speed control area S2. Then, the received light amount control unit 45 increases or decreases the exposure time in the shutter speed control area S2 in units of a block period.

In this case, although the pulse driving signal is no longer equally spaced pulses as shown by the two-dot chain line in FIG. 6, the pulse driving signal is repeatedly output in units of the block period tn that is n times the horizontal scanning period t. Accordingly, within the exposure time of each line set to the integral multiple of the block period tn, the integrated amount of received light by pulsed light is kept constant.

Next, the control of the shutter speed control area S2 will be described. The endoscope control unit 45 performs first pulse width control until the target amount of received light Ra is reached, and performs shutter speed control in the area where the target amount of received light is equal to or greater than Rb and less than Ra. In addition, as described above, when performing pulse number control in the area where the target amount of received light is less than Ra and equal to or greater than Ra1, shutter speed control is performed.

Figure 7:
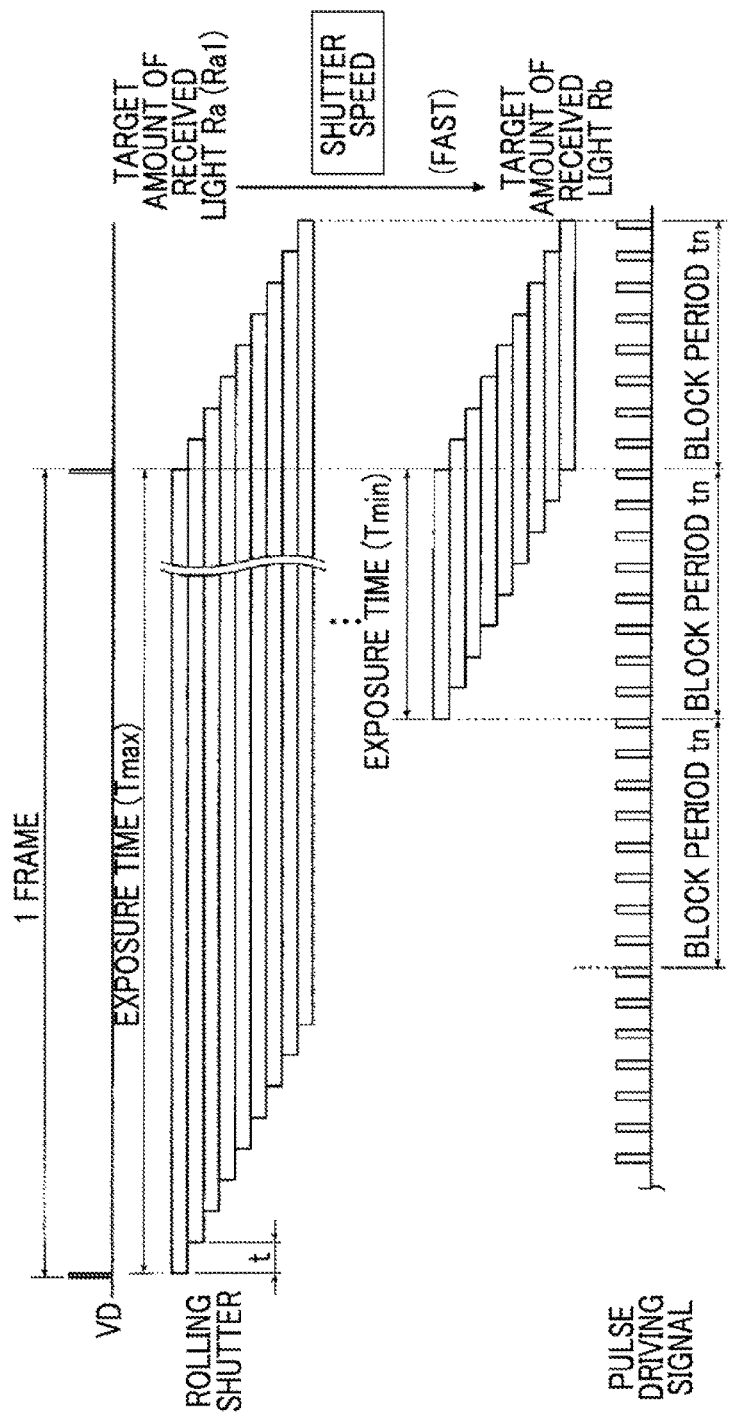
FIG. 7 is an explanatory diagram showing the relationship between the exposure time of the rolling shutter and the pulse driving signal in a shutter speed control area S2.

FIG. 7 is an explanatory diagram showing the relationship between the exposure time of the rolling shutter and the pulse driving signal in the shutter speed control area S2. The endoscope control unit 45 fixes the pulse driving signal to the state of the target amount of received light Ra in the area of the target amount of received light from Ra to Rb. Then, the exposure time of each line is changed with the horizontal scanning period t as a unit, and is set to the minimum exposure time Tmin, which is equal to the block period tn that is n times the horizontal scanning period t, in the target amount of received light Rb. An increase or decrease in the exposure time in this case is performed by back stuffing with the end timing of the exposure time as a reference.

Even if the endoscope control unit 45 controls an increase or decrease in the exposure time, the pulse of the pulse driving signal is controlled so as not to overlap the transition period of shutter opening and closing. Therefore, in the exposure time of each line, the integrated amount of received light by pulsed light is kept constant.

In addition, when the target amount of received light is set to Ra1 by the pulse number modulation described above, the endoscope control unit 45 increases or decreases the shutter speed with the block period tn, which is n times the horizontal scanning period t, as a unit. The shutter speed control in this case is performed by considering a part of the pulse number modulation performed between Ra and Ra1.

Next, the control of the pulse number control area S3 will be described. The endoscope control unit 45 performs shutter speed control until the target amount of received light Rb is reached, and performs pulse number control in the area where the target amount of received light is equal to or greater than Rc and less than Rb.

Figure 8:
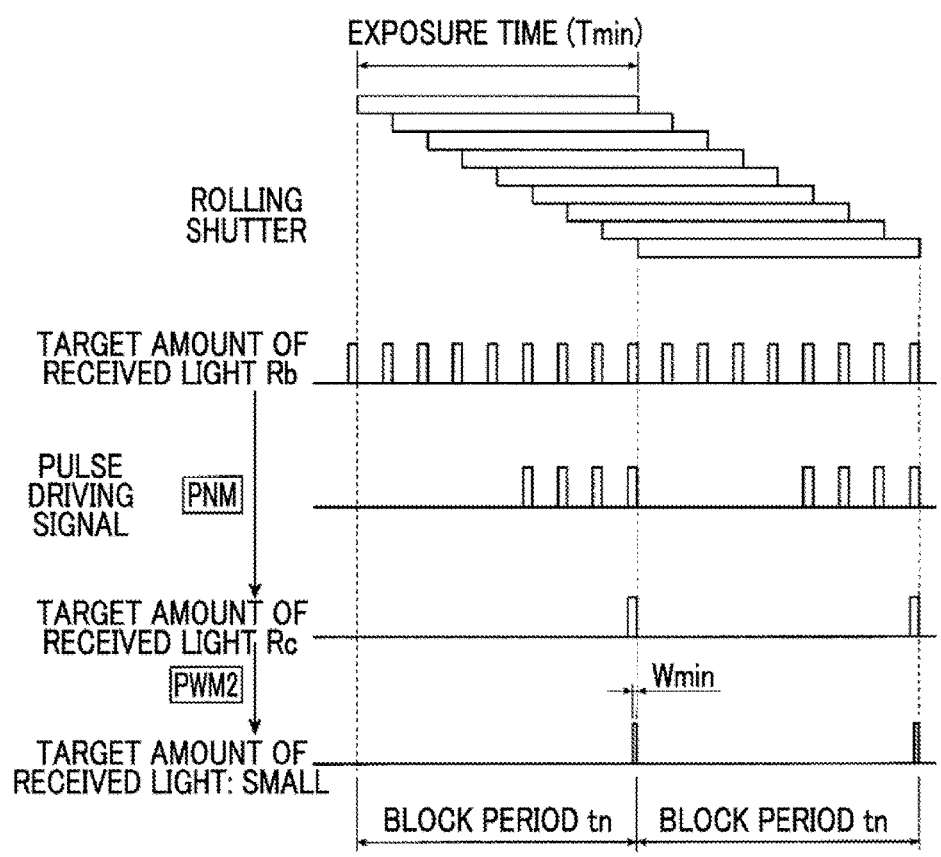
FIG. 8 is an explanatory diagram showing the relationship between the exposure time of the rolling shutter and the pulse driving signal in a pulse number control area (PNM) S3 and a second pulse width control area (PWM2) S4.

FIG. 8 is an explanatory diagram showing the relationship between the exposure time of the rolling shutter and the pulse driving signal in the pulse number control area (PNM) S3 and the second pulse width control area (PWM2) S4. The endoscope control unit 45 fixes the exposure time of each line to the minimum exposure time Tmin, which is equal to the block period tn, in the area of the target amount of received light from Rb to Rc. Then, pulse number control to reduce the number of pulses from the state of the target amount of received light Rb is performed on the pulse driving signal. In the target amount of received light Rc, the number of pulses is reduced down to one pulse in the block period tn.

When the target amount of received light is less than Rc, the endoscope control unit 45 performs second pulse width control to reduce the pulse width of the pulse driving signal in a state where the exposure time of each line is fixed to the minimum exposure time Tmin equal to the block period tn and the pulse driving signal of the light source 39 is thinned out.

In the pulse width modulation of the endoscope control unit 45, it is preferable to output the pulse of the pulse driving signal at a timing that does not overlap the transition period of shutter opening and closing of the imaging element 37.

Figure 9:
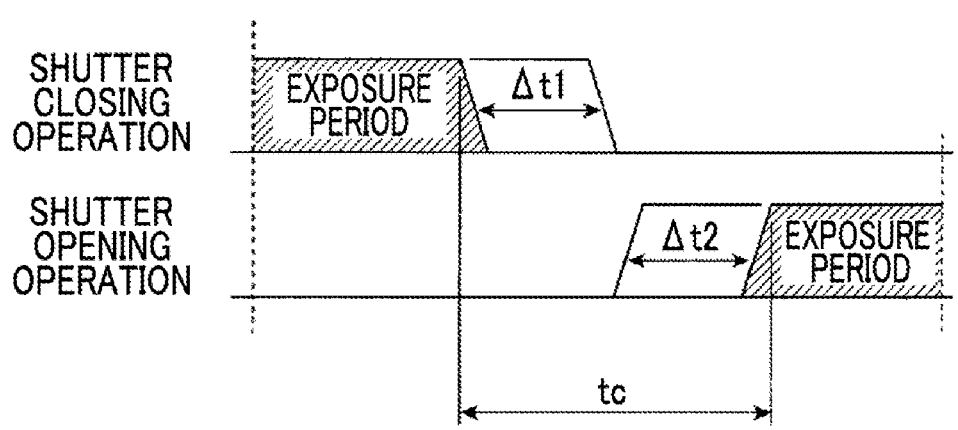
FIG. 9 is an explanatory diagram schematically showing the variations of the shutter closing operation and the shutter opening operation.

FIG. 9 is an explanatory diagram schematically showing the variations of the shutter closing operation and the shutter opening operation. The behavior of the shutter operation at the exposure end timing and exposure start timing of each line is not constant in all lines, and has a variation unique to each line, such as an end error $\Delta t1$ and a start error $\Delta t2$. Therefore, the endoscope control unit 45 performs control such that the pulse of the pulse driving signal is not input for the period tc with this variation.

Figure 10A:
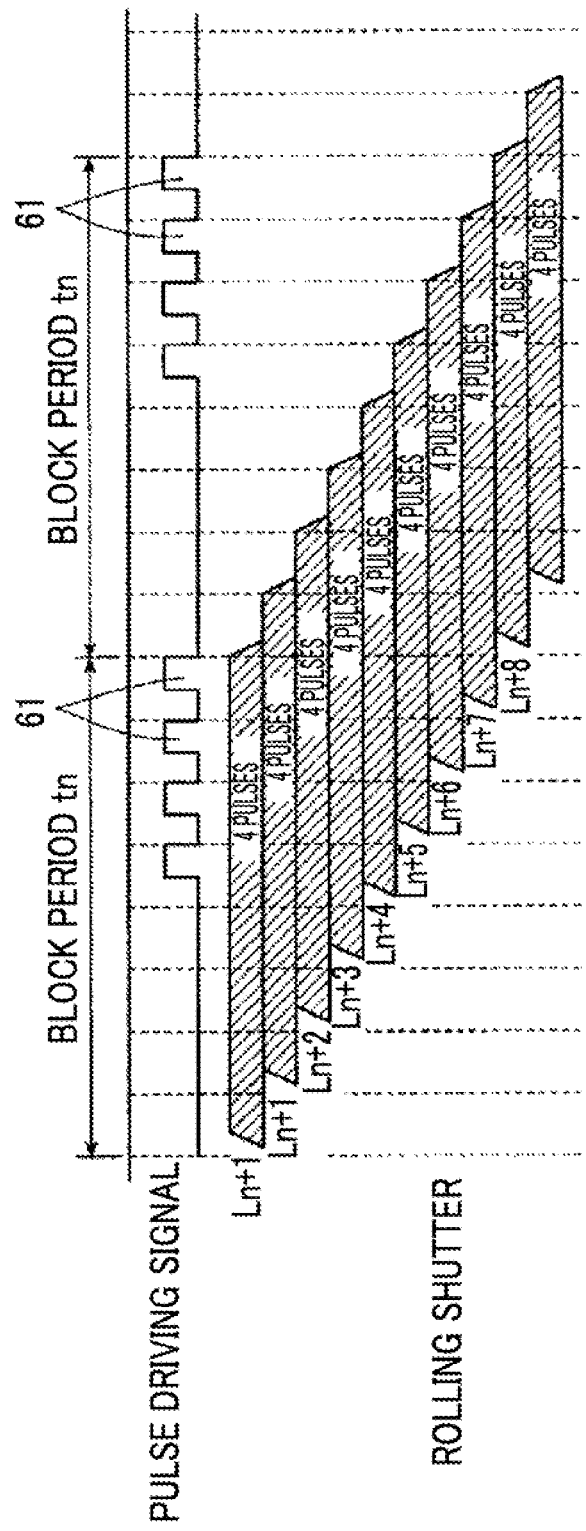
FIG. 10(A) is a timing chart showing a state in which the pulse width of each pulse of the pulse driving signal is increased or decreased by back stuffing with the exposure end timing of at least one line as a reference.

Specifically, as shown in FIG. 10(A), the endoscope control unit 45 increases or decreases the pulse width of each pulse of the pulse driving signal by back stuffing with the exposure end timing of at least one line as a reference. That is, the falling timing of a pulse 61 of the pulse driving signal is synchronized with the shutter closing timing of the rolling shutter.

In this manner, the number of received light pulses of the pulse driving signal in the exposure time of each line in this case becomes four pulses in all lines. As a result, the amount of received light becomes uniform.

Figure 10B:
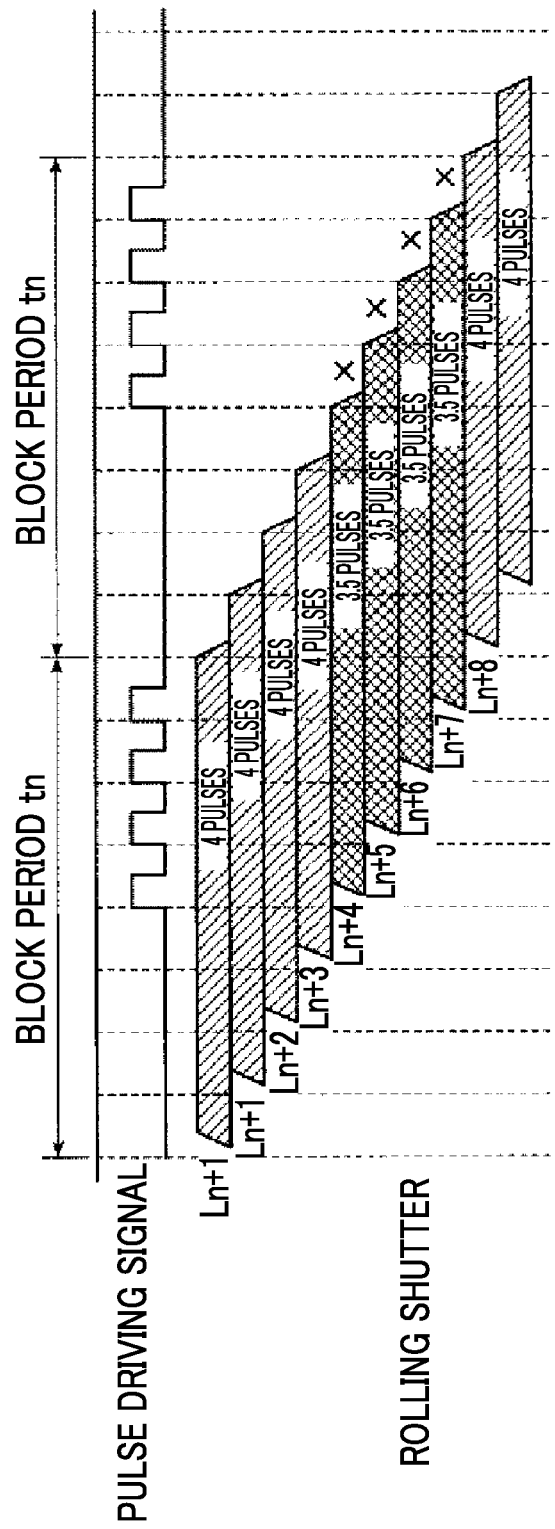
FIG. 10(B) is a timing chart showing a state in which the pulse width of each pulse of the pulse driving signal is increased or decreased by front stuffing with the exposure end timing of at least one line as a reference.

On the other hand, as shown in FIG. 10(B), when the pulse width of each pulse of the pulse driving signal is controlled by front stuffing with the exposure end timing of at least one line as a reference, lines of four pulses and lines of 3.5 pulses are mixed, and the number of received light pulses is not constant in all lines. This occurs because a pulse is present within a variation period Tc of the exposure time shown in FIG. 9 in a certain line.

Basically, the endoscope control unit 45 controls the pulse of the pulse driving signal so as not to be output within the transition period of shutter opening and closing as described above. However, in the first pulse width control area S1 and the shutter speed control area S2, the amount of error for the integrated amount of received light is small. Therefore, in at least the pulse number control area S3 and the second pulse width control area S4, the accuracy of the amount of exposure is not substantially lowered if the output timing of the pulse is controlled such that the pulse does not overlap the transition period of shutter opening and closing described above.

When increasing the target amount of received light from Rb, the endoscope control unit 45 may control the pulse width of the pulse driving signal without proceeding to the shutter speed control of S2, for example, until the target amount of received light reaches Rb1 from Rb. Thus, by extending the pulse modulation control as it is rather than switching the pulse modulation control to the shutter speed control, smoother dimming control becomes possible without switching an object to be controlled. That is, when changing the amount of received light across each control area of the received light amount control table shown in FIG. 4, hysteresis control may be performed in which different received light amount controls are performed in a case of changing from the large side to the small side of the target amount of received light and a case of changing from the small side to the large side.

For example, a plurality of received light amount control tables whose values of the amount of received light at the change point of each control area are different are prepared, and the target value of the amount of light emitted from the light source and the target value of the exposure time of the imaging element are determined with reference to the received light amount control tables that are switched according to the change direction of the amount of received light. Thus, control is performed by the combination of the different amounts of emitted light and different exposure times.

In addition, the received light amount control table includes an additional area for obtaining the same amount of received light, and control is performed by the combination of the different amount of emitted light and different exposure time by using the additional area only for one side of the change direction of the amount of received light.

As described above, according to the endoscope apparatus 100 having this configuration, the received light amount control unit performs pulse driving of the light source at a timing synchronized with a timing pulse signal having, as a period, 1/p of the exposure start timing interval when driving the imaging element using the rolling shutter method. By performing this control, it is not necessary to change the control of the pulse driving signal especially according to the shift of the exposure time due to the rolling shutter type imaging element. In addition, even if imaging is performed by illumination light from the light source, in which pulse lighting control of the amount of emitted light is performed, using the rolling shutter type imaging element, it is possible to stably obtain a high-quality image without illumination unevenness due to the exposure period of the imaging element that is different for each line.

In addition, a light source and an imaging element are controlled such that the pulse signal of the same pattern is output as a pulse driving signal of the light source having one block period, in which line blocks each including n lines obtained by dividing the total number L of horizontal pixel lines of the imaging element by m are arrayed in the vertical direction, as one period.

Therefore, also in the rolling shutter type imaging element in which the exposure timing of all pixels is not the same, it is possible to obtain a wide dimming dynamic range without causing trouble in light control. In addition, it is possible to perform received light amount control in which the width of the amount of received light that can be set is large. In addition, since the endoscope control unit performs the received light amount control by combining the control of the shutter speed in addition to the pulse driving of the light source, it is possible to increase the dimming resolution more than a case where dimming is performed only by pulse lighting control of the light source.

For example, even if comparison with a dimming dynamic range when performing light amount control using a white light source, such as a xenon lamp or a halogen lamp, and a mechanical shutter is performed, it is possible to realize received light amount control of a wide dimming dynamic range equal to or greater than the above dimming dynamic range. Therefore, a high-quality endoscopic image can always be acquired. In particular, in the endoscopic image, a diagnosis should be made from a subtle shadow image. Accordingly, an image having a dimming dynamic range wider than normal photographs and high dimming resolution is required for accurate medical diagnosis. According to the endoscope apparatus having this configuration, it is possible to provide high-quality observation image information that can meet such a demanding level of image quality.

Next, another configuration of the endoscope apparatus will be described.

Figure 11:
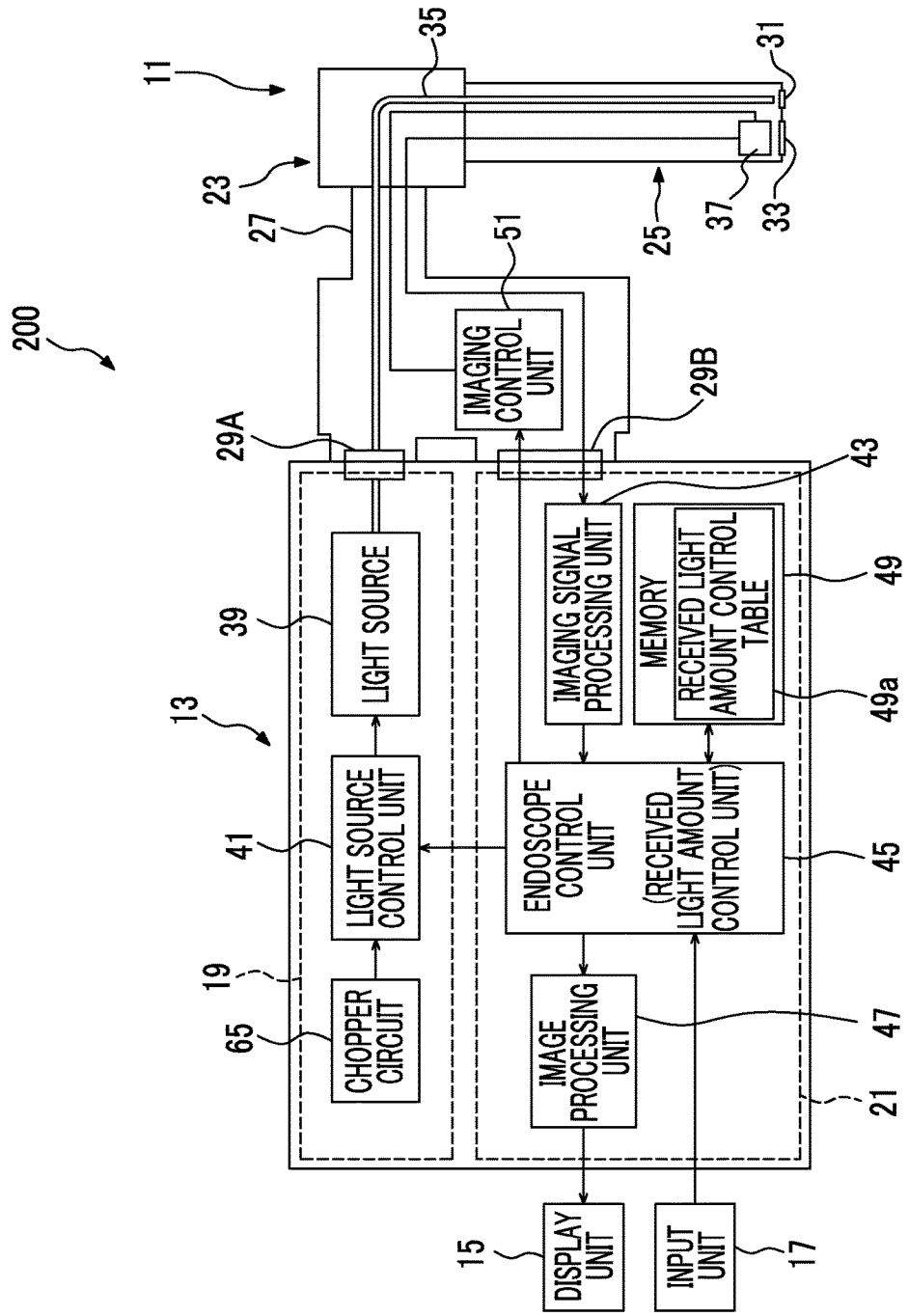
FIG. 11 is a block diagram showing the schematic configuration of another endoscope apparatus.

FIG. 11 is a block diagram showing the schematic configuration of an endoscope apparatus 200. The endoscope apparatus 200 is the same as the endoscope apparatus 100 shown in FIG. 1 except that a chopper circuit 65, which is connected to the light source control unit 41 and generates a driving signal of the light source 39, is provided to make the light source 39 remain lit continuously by a chopping pulse signal.

Figure 12:
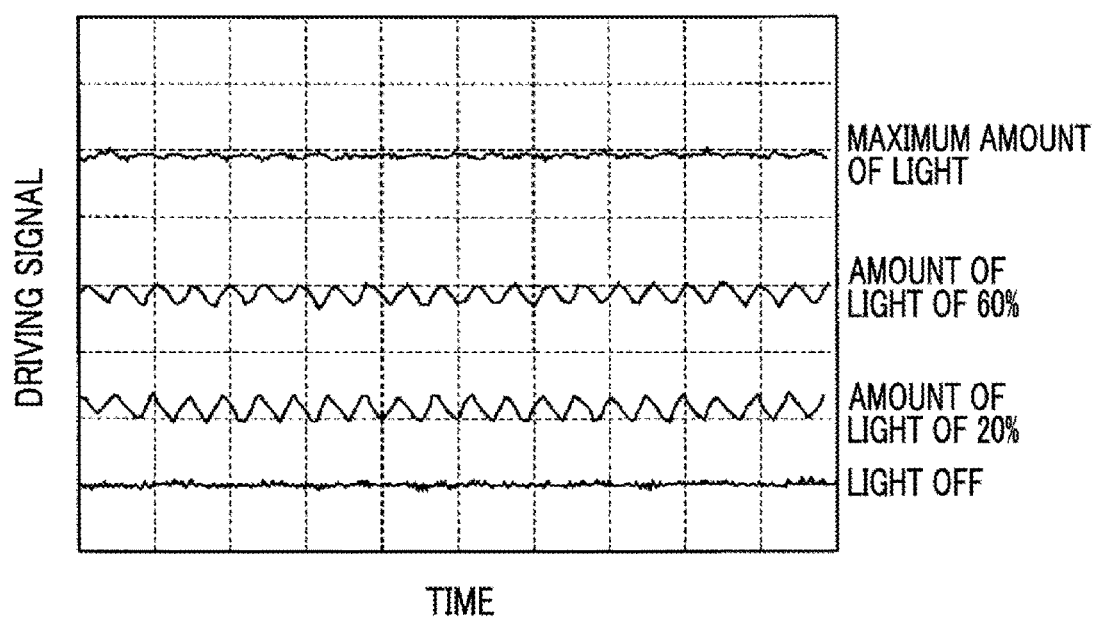
FIG. 12 is a graph showing the waveform of a driving signal from a chopper circuit with respect to the set amount of light.

The chopper circuit 65 generates a pulsation by chopping in the generated driving signal when a smoothing circuit constant is fixed. By this pulsation, the amount of light emitted from the light source 39 causes a pulsation of the light intensity corresponding to the pulsation of the driving signal. FIG. 12 shows the waveform of a driving signal from a chopper circuit with respect to the set amount of light. In a middle range between the maximum set light amount and unlit, a driving signal has a pulsation in which a bias component and a chopping pulse component are superimposed, as shown in the case of the amount of light of 20% or 60%. The waveform of this pulsation is smoothed as the set amount of light increases, and becomes almost flat at the maximum amount of light.

Figure 13:
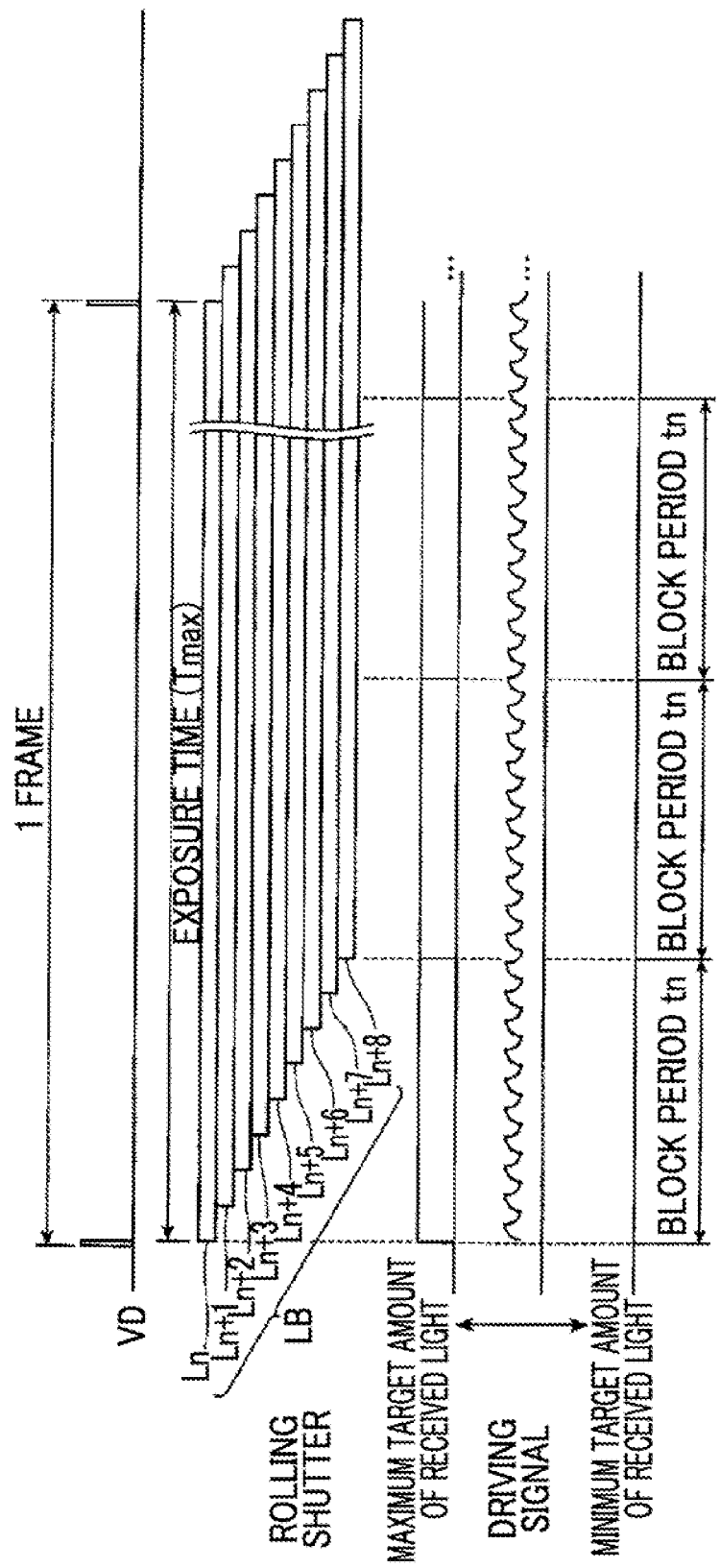
FIG. 13 is a timing chart showing the relationship between a driving signal and the timing of the exposure period of each line by the rolling shutter.

FIG. 13 shows the relationship between the driving signal and the timing of the exposure period of each line by the rolling shutter. In this configuration, the light source control unit 41 drives the light source 39 to emit light at all timings of the timing pulse signal. Similar to the case of the pulse modulation control described above, the light source 39 is driven at a timing synchronized with a timing pulse signal (driving signal) having 1/p of the exposure start timing interval of the imaging element as a period.

Figure 14:
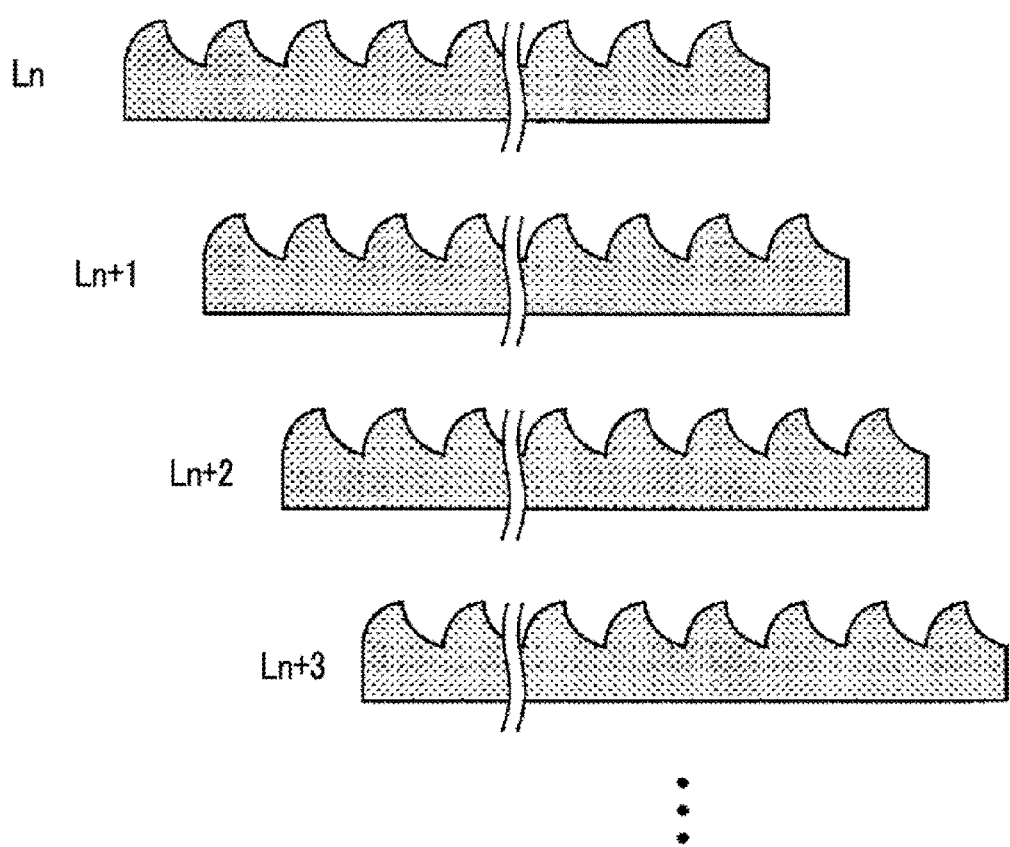
FIG. 14 is an explanatory diagram showing the waveform of the driving signal within the exposure time.

Therefore, according to the above-described driving, as shown in FIG. 14, the same number of pulsations are included in driving signals within the exposure time for the respective lines (Ln, Ln+1, . . . ) of the imaging element. For this reason, since the integrated intensity of the driving signal is equal in the respective lines, the amount of received light does not change. Therefore, it is possible to realize both a wide dimming dynamic range and high dimming resolution.

The present invention is not limited to the embodiment described above, and the respective components of the embodiment may be combined with each other or changes and applications of the present invention may be made by those skilled in the art based on the description of this specification and known techniques. These are also included in the range of the request for protection. Although the endoscope apparatus is illustrated in the example described above, the present invention is not limited thereto. According to the imaging device including at least the light source device 19, the processor 21, the imaging element 37, and the imaging control unit 51 shown in FIG. 1, it is possible to obtain a high-quality captured image having a wide dimming dynamic range and high dimming resolution as described above.

As described above, the following is disclosed in this specification.

(1) An imaging device including: a light source that emits light by pulse driving; a light source control unit that controls an amount of light emitted from the light source by performing pulse modulation driving of the light source; and an imaging unit that includes an imaging element, in which a plurality of pixels are arrayed in a horizontal direction and a vertical direction, and performs imaging by driving the imaging element using a rolling shutter method. The light source control unit performs pulse driving of the light source at a timing synchronized with a timing pulse signal having, as a period, 1/p (p is an integer of 1 or more) of an exposure start timing interval when driving the imaging element using the rolling shutter method.

(2) In the imaging device described in (1), the imaging unit performs scan driving of a horizontal pixel line, in which the pixels are aligned in the horizontal direction, sequentially from one end side of the horizontal pixel line in the vertical direction to the other end side, and performs driving by shifting an exposure start timing of each horizontal pixel line by a horizontal scanning period that is a period in which one horizontal pixel line is scanned. A received light amount control unit is further provided which has a received light amount control table in which a combination of the amount of light emitted from the light source and exposure time of the imaging element is matched with an assumed amount of received light that the imaging element receives in that case, determines a target value of the amount of light emitted from the light source and a target value of the exposure time of the imaging element with reference to the received light amount control table, and controls the light source control unit and the imaging unit based on the determined target value of the amount of emitted light and the determined target value of the exposure time. The light source control unit performs pulse driving of the light source using a pulse driving signal of the same pattern having, as one period, a block period that is an exposure start timing interval of a block in which line blocks, each of which includes n (n is an integer of 2 or more) lines obtained by dividing the total number L of horizontal pixel lines of the imaging element by m (m is an integer of 2 or more), are arrayed in the vertical direction.

(3) In the imaging device described in (2), the received light amount control table has at least a first pulse width control area matched with the amount of received light when the exposure time of the imaging element is fixed and a pulse width of the pulse driving signal of the light source is increased or decreased, a shutter speed control area matched with the amount of received light when the pulse width of the pulse driving signal of the light source is fixed and the exposure time of the imaging element is increased or decreased, a first pulse number control area matched with the amount of received light when the number of pulses of the pulse driving signal of the light source is increased or decreased in a state where the exposure time of the imaging element is fixed to an integral multiple of a block period obtained by multiplying the horizontal scanning period by n, and a second pulse width control area matched with the amount of received light when the pulse width of the pulse driving signal is increased or decreased in a state where the exposure time of the imaging element is fixed to an integral multiple of the block period and the pulse driving signal of the light source is thinned out.

(4) In the imaging device described in (3), the amount of received light in the received light amount control table decreases in an order of the first pulse width control area, the shutter speed control area, the first pulse number control area, and the second pulse width control area.

(5) In the imaging device described in (4), the light source control unit outputs the pulse driving signal in the first pulse number control area and the second pulse width control area at a timing that does not overlap a shutter opening and closing operation period of the imaging element.

(6) In the imaging device described in (5), the light source control unit increases or decreases the pulse width of the pulse driving signal in the first and second pulse width control areas by back stuffing with an exposure end timing of at least one of the horizontal pixel lines as a reference and outputs the pulse driving signal.

(7) In the imaging device described in any of (3) to (6), the exposure time of the imaging element in the first pulse width control area of the received light amount control table is a maximum exposure time of one frame.

(8) In the imaging device described in any of (3) to (7), the light source control unit outputs the pulse driving signal in the first pulse width control area with a maximum width of each pulse of the pulse driving signal in the first pulse width control area as the horizontal scanning period.

(9) In the imaging device described in any of (3) to (8), the light source control unit outputs the pulse driving signal by setting the number of pulses of the pulse driving signal within an exposure time of the horizontal pixel line to the same number of pulses for all of the horizontal pixel lines.

(10) In the imaging device described in any of (3) to (9), the received light amount control unit increases or decreases the exposure time in the shutter speed control area in units of the horizontal scanning period.

(11) In the imaging device described in any of (4) to (10), the received light amount control table further includes a second pulse number control area matched with the amount of received light when the number of pulses of the pulse driving signal of the light source is increased or decreased in a state where the exposure time of the imaging element is fixed to the same exposure time as an exposure time in the first pulse width control area and the pulse width of the pulse driving signal of the light source is fixed. The amount of received light in the second pulse number control area is between the amount of received light in the first pulse width control area and the amount of received light in the shutter speed control area. The received light amount control unit increases or decreases the exposure time in the shutter speed control area in units of the block period.

(12) In the imaging device described in any of (3) to (11), the received light amount control unit has a plurality of received light amount control tables whose values of the amount of received light at a change point of each control area are different, and determines a target value of the amount of light emitted from the light source and a target value of the exposure time of the imaging element with reference to the received light amount control tables that are different according to a change direction of the amount of received light of the imaging element.

(13) In the imaging device described in (1), the light source control unit drives the light source to emit light at all timings of the timing pulse signal.

(14) In the imaging device described in any of (1) to (13), the light source is a semiconductor light emitting element.

(15) An endoscope apparatus including the imaging device according to any one of (1) to (14).

What is claimed is:
1. An imaging device, comprising:
   a light source that emits light by pulse driving;
   a light source control unit that controls an amount of light emitted from the light source by performing pulse modulation driving of the light source; and
   an imaging unit that includes an imaging element, in which a plurality of pixels are arrayed in a horizontal direction and a vertical direction, and performs imaging by driving the imaging element using a rolling shutter method,
   wherein the light source control unit performs pulse driving of the light source at a timing synchronized with a timing pulse signal having, as a period, when p is an integer of 1 or more, 1/p of an exposure start timing interval when driving the imaging element using the rolling shutter method,
   wherein the imaging unit performs scan driving of a horizontal pixel line, in which the pixels are aligned in the horizontal direction, sequentially from one end side of the horizontal pixel line in the vertical direction to the other end side, and performs driving by shifting an exposure start timing of each horizontal pixel line by a horizontal scanning period that is a period in which one horizontal pixel line is scanned, a received light amount control unit is further provided which has a received light amount control table in which a combination of the amount of light emitted from the light source and an exposure time of the imaging element is matched with an assumed amount of received light that the imaging element receives in that case, determines a target value of the amount of light emitted from the light source and a target value of the exposure time of the imaging element based on the assumed amount of received light that the imaging element receives with reference to the received light amount control table, and controls the light source control unit and the imaging unit based on the determined target value of the amount of emitted light and the determined target value of the exposure time, and the light source control unit performs pulse driving of the light source using a pulse driving signal of the same pattern having, as one period, a block period that is an exposure start timing interval of a block in which line blocks, each of which includes n lines obtained by dividing the total number L of horizontal pixel lines of the imaging element by m, when both n and m are integers of 2 or more, are arrayed in the vertical direction.

2. The imaging device according to claim 1,
wherein the received light amount control table has at least a first pulse width control area matched with the amount of received light when the exposure time of the imaging element is fixed and a pulse width of the pulse driving signal of the light source is increased or decreased, a shutter speed control area matched with the amount of received light when the pulse width of the pulse driving signal of the light source is fixed and the exposure time of the imaging element is increased or decreased, a first pulse number control area matched with the amount of received light when the number of pulses of the pulse driving signal of the light source is increased or decreased in a state where the exposure time of the imaging element is fixed to an integral multiple of a block period obtained by multiplying the horizontal scanning period by n, and a second pulse width control area matched with the amount of received light when the pulse width of the pulse driving signal is increased or decreased in a state where the exposure time of the imaging element is fixed to an integral multiple of the block period and the pulse driving signal of the light source is thinned out.

3. The imaging device according to claim 2,
wherein the amount of received light in the received light amount control table decreases in an order of the first pulse width control area, the shutter speed control area, the first pulse number control area, and the second pulse width control area.

4. The imaging device according to claim 3,
wherein the light source control unit outputs the pulse driving signal in the first pulse number control area and the second pulse width control area at a timing that does not overlap a shutter opening and closing operation period of the imaging element.

5. The imaging device according to claim 4,
wherein the light source control unit increases or decreases the pulse width of the pulse driving signal in the first and second pulse width control areas by back stuffing with an exposure end timing of at least one of the horizontal pixel lines as a reference and outputs the pulse driving signal.

6. The imaging device according to claim 5,
wherein the exposure time of the imaging element in the first pulse width control area of the received light amount control table is a maximum exposure time of one frame.

7. The imaging device according to claim 5,
wherein the light source control unit outputs the pulse driving signal in the first pulse width control area with a maximum width of each pulse of the pulse driving signal in the first pulse width control area as the horizontal scanning period.

8. The imaging device according to claim 4,
wherein the exposure time of the imaging element in the first pulse width control area of the received light amount control table is a maximum exposure time of one frame.

9. The imaging device according to claim 4,
wherein the light source control unit outputs the pulse driving signal in the first pulse width control area with a maximum width of each pulse of the pulse driving signal in the first pulse width control area as the horizontal scanning period.

10. The imaging device according to claim 3,
wherein the exposure time of the imaging element in the first pulse width control area of the received light amount control table is a maximum exposure time of one frame.

11. The imaging device according to claim 3,
wherein the light source control unit outputs the pulse driving signal in the first pulse width control area with a maximum width of each pulse of the pulse driving signal in the first pulse width control area as the horizontal scanning period.

12. The imaging device according to claim 3,
wherein the received light amount control table further includes a second pulse number control area matched with the amount of received light when the number of pulses of the pulse driving signal of the light source is increased or decreased in a state where the exposure time of the imaging element is fixed to the same exposure time as an exposure time in the first pulse width control area and the pulse width of the pulse driving signal of the light source is fixed, the amount of received light in the second pulse number control area is between the amount of received light in the first pulse width control area and the amount of received light in the shutter speed control area, and the received light amount control unit increases or decreases the exposure time in the shutter speed control area in units of the block period.

13. The imaging device according to claim 2,
wherein the exposure time of the imaging element in the first pulse width control area of the received light amount control table is a maximum exposure time of one frame.

14. The imaging device according to claim 2,
wherein the light source control unit outputs the pulse driving signal in the first pulse width control area with a maximum width of each pulse of the pulse driving signal in the first pulse width control area as the horizontal scanning period.

15. The imaging device according to claim 2,
wherein the light source control unit outputs the pulse driving signal by setting the number of pulses of the pulse driving signal within an exposure time of the horizontal pixel line to the same number of pulses for all of the horizontal pixel lines.

16. The imaging device according to claim 2, wherein the received light amount control unit increases or decreases the exposure time in the shutter speed control area in units of the horizontal scanning period.

17. The imaging device according to claim 2, wherein the received light amount control unit has a plurality of received light amount control tables whose values of the amount of received light at a change point of each control area are different, and determines a target value of the amount of light emitted from the light source and a target value of the exposure time of the imaging element with reference to the received light amount control tables that are different according to a change direction of the amount of received light of the imaging element.

18. The imaging device according to claim 1, wherein the light source control unit drives the light source to emit light at all timings of the timing pulse signal.

19. The imaging device according to claim 1, wherein the light source is a semiconductor light emitting element.

20. An endoscope apparatus, comprising:
the imaging device according to claim 1.

* * * * *